(12) United States Patent
Dadi

(10) Patent No.: US 7,654,823 B2
(45) Date of Patent: Feb. 2, 2010

(54) METHOD AND DEVICE FOR DETERMINING POSITION OF DENTAL IMPLANTS

(75) Inventor: Michel Dadi, 9 Shlomzion HaMalka St., Tel-Aviv, 62267 (IL)

(73) Assignee: Michel Dadi, Tel-Aviv (IL)

( * ) Notice: Subject to any disclaimer, the term of this patent is extended or adjusted under 35 U.S.C. 154(b) by 64 days.

(21) Appl. No.: 11/530,017

(22) Filed: Sep. 7, 2006

(65) Prior Publication Data

US 2007/0059661 A1    Mar. 15, 2007

Related U.S. Application Data

(63) Continuation of application No. 10/771,130, filed on Feb. 3, 2004, now Pat. No. 7,104,795.

(60) Provisional application No. 60/444,671, filed on Feb. 4, 2003.

(51) Int. Cl.
 *A61C 19/04* (2006.01)
 *A61C 8/00* (2006.01)
(52) U.S. Cl. ................................ 433/72; 433/75; 433/173
(58) Field of Classification Search .................... 433/72, 433/75–76, 173–176
 See application file for complete search history.

(56) References Cited

U.S. PATENT DOCUMENTS

| | | | |
|---|---|---|---|
| 3,906,634 A | 9/1975 | Aspel | |
| 4,325,373 A | 4/1982 | Slivenko et al. | |
| 4,364,381 A | 12/1982 | Sher et al. | |
| 4,439,152 A | 3/1984 | Small | |
| 4,571,180 A | 2/1986 | Kulick | |
| 4,961,674 A | 10/1990 | Wang et al. | |
| 4,998,881 A | 3/1991 | Lauks | |
| 5,176,516 A * | 1/1993 | Koizumi | 433/72 |
| 5,246,370 A | 9/1993 | Coatoam | |
| 5,312,409 A | 5/1994 | Mclaughlin et al. | |
| 5,556,278 A | 9/1996 | Meitner | |
| 5,575,656 A | 11/1996 | Hajjar | |
| 5,613,852 A | 3/1997 | Bavitz | |
| 5,636,986 A | 6/1997 | Pezeshkian | |
| 5,688,283 A | 11/1997 | Knapp | |
| 5,718,579 A | 2/1998 | Kennedy | |
| 5,725,376 A | 3/1998 | Poirier | |
| 5,733,124 A | 3/1998 | Kwan | |
| 5,743,916 A | 4/1998 | Greenberg et al. | |
| 5,791,902 A | 8/1998 | Lauks | |
| 5,800,168 A | 9/1998 | Cascione et al. | |

(Continued)

*Primary Examiner*—John J Wilson

(57) ABSTRACT

An accessory for use in aiding an oral surgeon to determine the optimum position and angle for a dental implant to be installed in a bone includes a probe assembly having one or more pairs of probe members pivotally mounted to each other about a pivot axis at their centers. Each pair of probe members is configured and dimensioned such that one end of the pair on one side of the pivot axis serves as a probe end to straddle the bone with their tips contacting the bone at opposed contact points thereon, and the opposite end of the pair on the opposite side of the pivot axis serves as a guide end in which the tips of the probe members are automatically located to indicate the thickness of the bone at the pair of opposed contact points. Also described are a kit including a plurality of such accessories, a tool for manually applying such accessories, and a method of using such accessories for use in determining the optimum position and angle for a dental implant.

7 Claims, 8 Drawing Sheets

U.S. PATENT DOCUMENTS

| | | |
|---|---|---|
| 5,888,034 A | 3/1999 | Greenberg |
| 5,915,962 A | 6/1999 | Rosenlicht |
| 5,927,982 A | 7/1999 | Kruger |
| 5,954,769 A | 9/1999 | Rosenlicht |
| 5,984,681 A | 11/1999 | Huang |
| 5,989,025 A | 11/1999 | Conley |
| 5,989,258 A | 11/1999 | Hattori |
| 6,000,939 A * | 12/1999 | Ray et al. .................... 433/27 |
| 6,068,479 A | 5/2000 | Kwan |
| 6,099,313 A | 8/2000 | Dorken et al. |
| 6,319,006 B1 | 11/2001 | Scherer et al. |
| 6,382,975 B1 | 5/2002 | Poirier |
| 6,610,079 B1 | 8/2003 | Li et al. |
| 6,755,652 B2 | 6/2004 | Nanni |
| 6,783,359 B2 | 8/2004 | Kapit |
| 6,793,491 B2 | 9/2004 | Klein et al. |
| 6,814,575 B2 | 11/2004 | Poirier |
| 7,104,795 B2 | 9/2006 | Dadi |
| 2004/0259051 A1 | 12/2004 | Brajnovic |

* cited by examiner

METHOD AND DEVICE FOR DETERMINING POSITION OF DENTAL IMPLANTS

PRIORITY INFORMATION

This application is a continuation/division of, and claims the benefit of priority under 35 U.S.C. §120 to, U.S. Pat. No. 7,104,795 issued Sep. 12, 2006, filed as U.S. patent application Ser. No. 10/771,130 on Feb. 3, 2004, and which in turn claims the benefit of priority under U.S.C. § 119(e) to Provisional Patent Application No. 60/444,671 filed Feb. 4, 2003.

BACKGROUND OF THE INVENTION

1. Field of the Invention

The present invention relates generally to the field of dental implants, and more particularly to methods and devices for installing dental implants.

2. Description of the Related Art

Implant dentistry involves the restoration of one or more teeth in a patient's mouth using artificial components. Such artificial components typically include a dental implant and a prosthetic tooth and/or a final abutment that is secured to the dental implant. Generally, the process for restoring a tooth is carried out in three stages.

Stage I involves implanting the dental implant into the alveolar bone (i.e., jawbone) of a patient. The surgeon first accesses the alveolar bone through the patient's gum tissue and removes any remains of the tooth to be replaced. Next, the specific site in the alveolar bone where the implant will be anchored is prepared by drilling and/or reaming to accommodate the width of the dental implant to be inserted. Then, the dental implant is inserted into the hole, typically by screwing, although other techniques are known for introducing the implant in the jawbone.

After the implant is initially installed in the bone, a temporary healing cap is secured over the exposed proximal end in order to seal an internal bore of the implant. The patient's gums are then sutured over the implant to allow the implant site to heal and to allow desired osseointegration to occur. Complete osseointegration typically takes anywhere from three to ten months.

During stage II, the surgeon reaccesses the implant fixture by making an incision through the patient's gum tissues. The healing cap is then removed, exposing the proximal end of the implant. Typically, an impression coping is attached to the implant and a mold or impression is then taken of the patient's mouth to accurately record the position and orientation of the implant within the mouth. This is used to create a plaster model or analogue of the mouth and/or the implant site and provides the information needed to fabricate the prosthetic replacement tooth and any required intermediate prosthetic components. Stage II is typically completed by attaching to the implant a temporary healing abutment or other transmucosal component to control the healing and growth of the patient's gum tissue around the implant site. In a modified procedure, an abutment or other transmucosal component is either integrally formed with the implant or attached to the implant during stage I. In such a procedure, stages I and II are effectively combined in to a single stage.

Stage III involves fabricating and placement of a cosmetic tooth prosthesis to the implant fixture. The plaster analogue provides laboratory technicians with a model of the patient's mouth, including the orientation of the implant fixture and/or abutment relative to the surrounding teeth. Based on this model, the technician constructs a final restoration. The final step in the restorative process is replacing the temporary healing abutment with the final abutment and attaching a final prosthesis to the final abutment.

With respect to Stage I, when an oral surgeon installs the dental implant, it is important that the dental implant is installed at a proper or optimum position and angle with respect to the particular structure of the alveolar bone that is receiving the implant. If the implant installed at an improper or non-optimum angle or position, the bone may not provide the required support, which may result in failure of the dental prostheses supported by the implant. Improper or non-optimum positioning may also result in a visually perceptible defect in the appearance of the dental prosthesis. Accordingly, it is important for the dental surgeon to be able to determine the proper or optimum position and angle for the dental implant. Many techniques and devices have been developed and used by oral surgeons, including radiographic examination, diagnostic casts, etc., for determining the optimum position and angle for the dental implant. However, such techniques tend to depend on the skill and experience of the oral surgeon.

SUMMARY OF THE INVENTION

Therefore, there remains a general need for an improved device and method for determining the proper or optimum position and angle of a dental implant with respect to the structure of the alveolar bone.

Accordingly, one embodiment of the present invention provides a dental implant guide which may used to aid oral surgeons in determining the optimum position and angle for a dental implant to be installed in a bone, by presenting the oral surgeon with a simplified view of the permitted limits for the dental implant. In one embodiment of use, the implant guide may be used without opening a flap in the gum tissue of the patient. In another embodiment of the invention, a plurality of such accessories may be provided in a kit, which may include a tool for applying such accessories to a patient's bone. Another embodiment relates to a method of using such accessories in determining the optimum position and angle for a dental implant.

In another embodiment of the present invention, there is provided a dental implant guide for aiding an oral surgeon in determining the optimum position and angle for a dental implant to be installed in a bone. The dental implant guide comprises a probe assembly including at least one pair of probe members pivotally mounted to each other about a pivot axis. The pair of probe members are configured and dimensioned such that one end of the probe assembly on one side of the pivot axis serves as a probe end in which the probe members of the pair may be configured to straddle the bone with their tips contacting the bone at opposed contact points thereon. The opposite end of the probe assembly on the opposite side of the pivot axis serves as a guide end in which the tips of the probe members are automatically located to indicate the thickness of the bone at the pair of opposed contact points. In a preferred embodiment, the opposite ends of the probe assembly are substantially symmetric with respect to the pivot axis.

In another embodiment of the present invention, there is provided an accessory for aiding an oral surgeon in determining the optimum position and angle for a dental implant to be installed in a bone. The accessory comprises a probe assembly including at least two pairs of probe members pivotally mounted to each other about a common pivot axis. The probe members of each pair are configured and dimensioned such that one end of the pair of probe members on one side of the pivot axis serves as a probe end in which the probe members of the pair may be located to straddle the bone with their tips contacting the bone at opposed contact points thereon. The opposite end of the probe members of the pair on the opposite side of the pivot axis serves as a guide end in which the tips of the probe members are automatically located to indicate the thickness of the bone at the pair of opposed contact points. The probe members of one pair are of a different length between their tips than the probe members of the other pair, such that the tips at the opposite ends of the probe members will be automatically located to indicate the thickness of the bone at two pairs of contact points, and thereby the contour of the bone in the region of the contact points. The accessory thus presents to the oral surgeon a simplified view of the permitted limits for the dental implant. In one embodiment of use, this may be done before opening a flap. In one preferred embodiment, the opposite ends of the probe members are substantially symmetric with respect to the pivot axis.

In a modified embodiment, each of the probe members is of substantially S-shaped configuration. Each probe member of one pair is biased towards the other probe member of the respective pair by a biasing member. In another modified embodiment, the assembly further includes a simulated tooth adjustably mounted with respect to the pivot axis to simulate a tooth to be fixed by the dental implant. The simulated tooth is mounted with respect to the pivot axis for adjustment longitudinally, transversely, and/or angularly, with respect to the bone to receive the implant, and is formed with holes therethrough to indicate the limits of the drill axis of the implant. The holes may also be used for drilling the bone, and the simulated tooth may also be provided with an indicator pin to indicate the drilling axis.

In another embodiment of the invention, the accessory includes two or more of the probe assemblies to be applied at spaced locations of a bone to thereby enable determination of the optimum position and angle for the dental implant in the section of the bone between the spaced locations.

According to another embodiment of the present invention, there is provided a kit including a plurality of accessories as in one or more of the embodiments described above. Such a kit preferably also includes a manual tool for applying each probe assembly to a bone of a patient to receive a dental implant. The manual tool includes a pair of pivotally mounted members each having a finger at one side of the pivot mounting, and a hand grip at the opposite side of the pivot mounting; and a biasing member to urge the hand-grips away from each other, and thereby the fingers towards each other.

In another embodiment of the present invention, there is provided a method of aiding an oral surgeon to determine the optimum position and angle for a dental implant to be installed in a bone. The method comprises applying to the bone a probe assembly, as described above, such that the probe end of the probe assembly straddles the bone and their tips contact the bone at opposed contact points thereon and utilizing the tips of the guide end of the probe assembly for indicating the permitted limits for the dental implant to be installed in the bone. In one embodiment, the permitted limits are defined, at least in part, by indicator points that are substantially symmetric to the opposed contact points.

In another embodiment of the invention, there is provide a method of determining the proper position and angle for a dental implant to be installed in a bone, comprising determining the contour of the jawbone at an insertion site of the dental implant; creating a substantially symmetrical image of the contour of the jawbone, the image being positioned above said insertion site, and using the substantially symmetrical image to determine the proper position and angle for a dental implant.

As will be described more particularly below, an advantage of certain embodiments of the present invention is that they may be used to present to the oral surgeon a simplified view of the permitted limits for the dental implant without even opening a flap in the patient's gum tissue. Such a view better enables the oral surgeon to determine the optimum position and angle for a dental implant to be installed in order to provide maximum support for the dental prosthesis to be later applied, as well as to minimize the possibility of producing a visually defective appearance in the dental prosthesis.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiments disclosed.

BRIEF DESCRIPTION OF THE DRAWINGS

These and other features of this invention will now be described with reference to the drawings of a preferred embodiment which is intended to illustrate and not to limit the invention. The drawings contain the following figures.

DETAILED DESCRIPTION OF THE PREFERRED EMBODIMENTS

Various embodiments of a dental implant guide will now be described. As will be explained in detail below, in certain embodiments, the dental implant guide aids an oral surgeon in determining the optimum position and/or angle for installation of a dental implant into a patient's jawbone. In a preferred embodiment, this is done by presenting the oral surgeon with a simplified view of the permitted limits or envelope that the jawbone provides for the dental implant. Advantageously, this may be done even before opening a flap in the patient's gum tissue.

In one embodiment, the dental implant guide comprises at least two probe points that are configured to probe the jawbone below the insertion site of the dental implant. The dental implant guide also comprises at least two indicator points that are configured to lie above the jawbone at the insertion site. The dental implant guide is configured such the position of the probe points is translated to the indicator points. In this manner, as the probe points expand and contract in response to the shape of the jawbone, the indicator points, in turn, expand and contract to provide to provide an indication of the shape of the jawbone at the insertion site. In one embodiment, the indication provides a general representation or approximate guide as to the contour of the jawbone. In another embodiment, the indication provides a more accurate and/or complete representation. In yet another embodiment, the dental implant guide creates a substantially symmetrical image of a slice of the bone in which the dental implant is to be inserted. The symmetrical image is preferably centered in the middle of the crest of the jawbone. In one such embodiment, the indicator points and probe points may move symmetrically about a point preferably centered in the middle of the crest of the jawbone such that the position of each one of the indicator points corresponds to the position of a corresponding probe point positioned on the opposite side of the jawbone.

Figure 1:
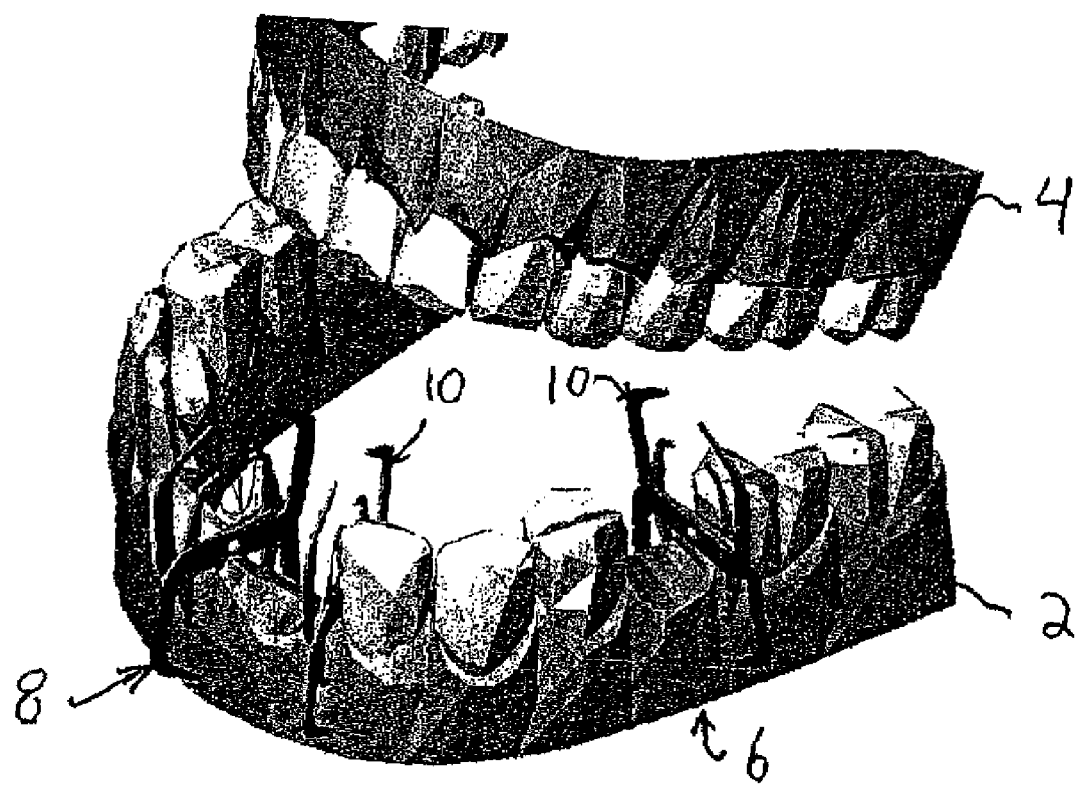
FIG. 1 is a side perspective view of a patient's mouth and an exemplary embodiment of two dental implant guides.

Turning now to a particular exemplary embodiment, FIG. 1 is a schematic illustration of a patient's mouth, which includes a movable lower jaw bone or mandible 2, and a fixed upper jaw bone or maxilla 4. For purposes of example, FIG. 1 also illustrates two implantation sites 6, 8 in the mandible 2. The first site 6 is for receiving a single tooth prosthetic device, which typically utilizes a single implant. The second site 8 is for receiving a prosthetic device that typically requires two (or more) prosthetic teeth to be fixed by two (or more) implants. In the description below, reference will be made to positions "above the insertion or implantation site." However, it should be appreciated that the term "above the insertion or implant site" will also refer to positions "below" implantation sites on the upper jaw bone or maxilla 4. That is, above or below refer to the space generally overlying the insertion or implantation site.

FIG. 1 also illustrate a pair of exemplary dental implant guides each generally designated with the reference 10 and to be described in detail below. As mentioned above, the tool guides 10 may be used to aid an oral surgeon in determining the optimum position and angle for installation of the dental implants (not shown) that are to be implanted at the first and second sites 6, 8.

Figure 2:
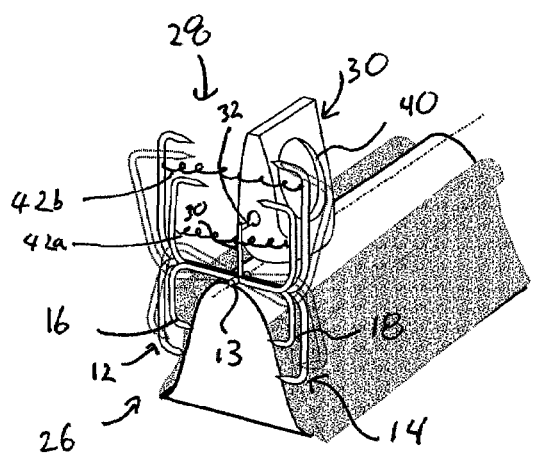
FIG. 2 is a side perspective view of another embodiment of a dental implant guide.
Figure 3:
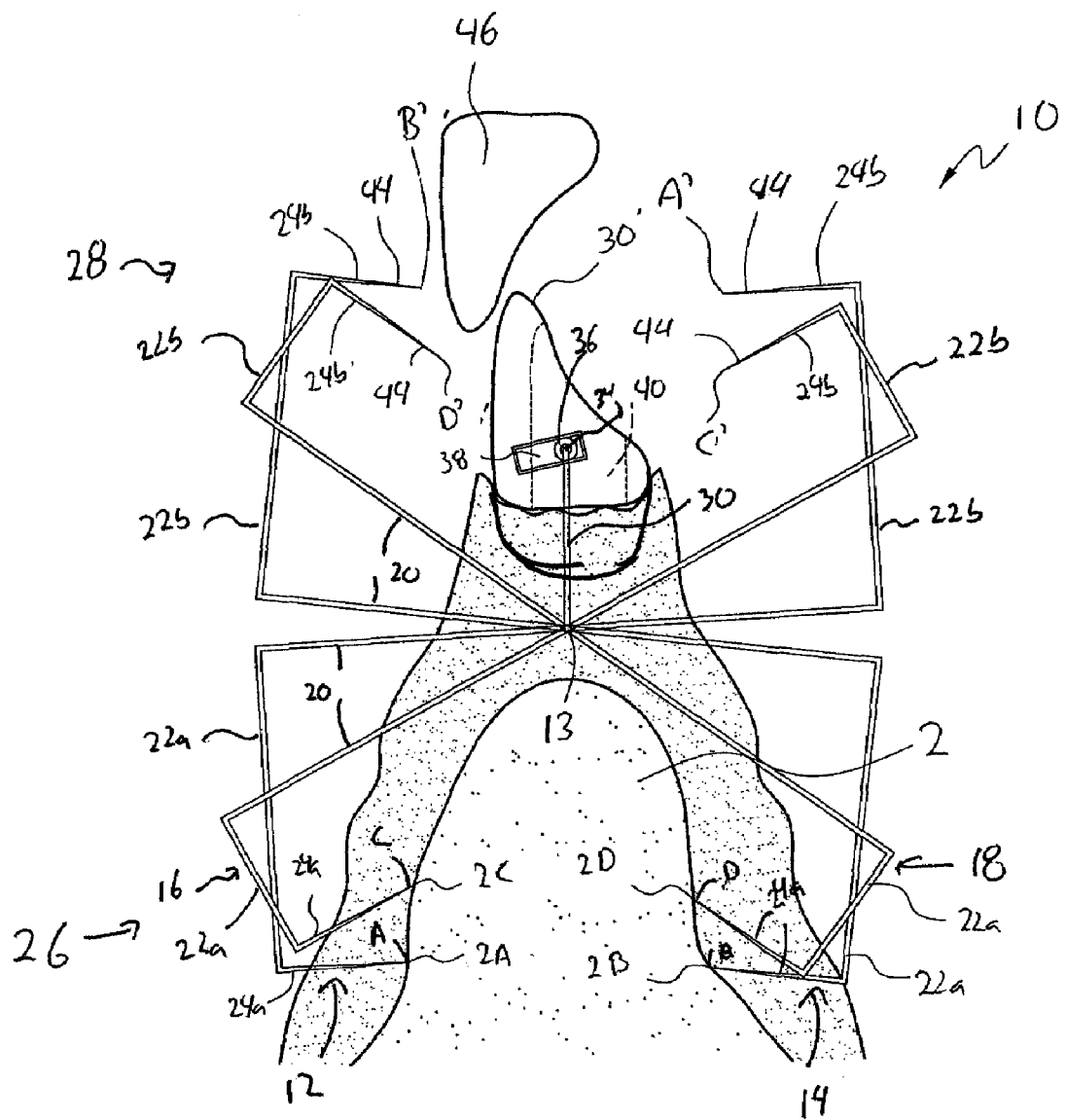
FIG. 3 is a side view of the dental implant guide of FIG. 2.

FIGS. 2 and 3 illustrate a slightly modified embodiment of the tool guide 10 of FIG. 1. In this embodiment, the tool guide 10 comprises at least a first pair of probe members 12, 14 that are pivotally mounted to each other on a pivot shaft 13 that preferably passes through the centers of the probe members 12, 14. The exemplary embodiment also includes a second pair of probe members 16, 18 that may be also pivotally mounted to each other on the pivot shaft 13. The second pair of probe members 16, 18 preferably have a shorter height (i.e., distance from the pivot shaft 13) than the first pair of probe members 12, 14.

Figure 3A:
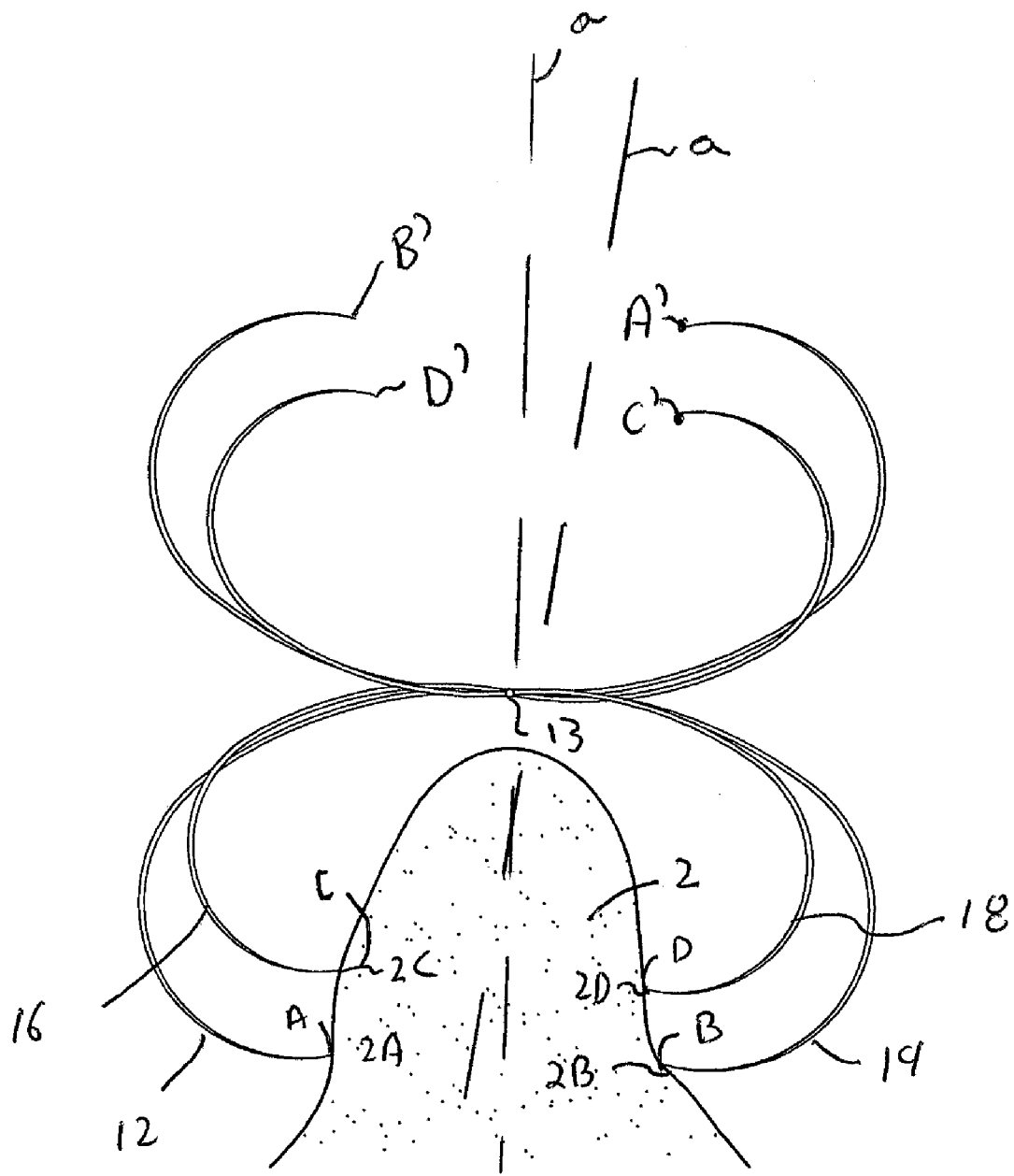
FIG. 3A is a side view of a modified embodiment of a dental implant guide.

With particularly reference to FIG. 3, in the exemplary embodiment, each of the probe members 12, 14, 16, 18 has a substantially S-configuration comprising a main portion 20 through which the pivot shaft 13 extends, a pair of secondary portions 22a, 22b, which extend in opposite directions away from the pivot shaft 13, and a pair of tertiary portions 24a, 24b, which extend in opposite directions towards the pivot shaft 13. In the illustrated embodiment, the secondary portion 22a, 22b, form a substantially 90 degree angle with respect to the main portion 20 and the tertiary portions 24a, 24b forms a substantially 90 degree angle with respect to the secondary portions 22a, 22b. In modified embodiments, the probe members 12, 14, 16, 18 may have a substantially different shape that may include more or less portions, curved sections and/or different angular orientations between the segments. For example, FIG. 3A illustrates an embodiment where the probe members 12', 14', 16', 18' are formed from curved segments. FIG. 1 illustrates an embodiment where the angle between the tertiary portion 24a, 24b and the secondary portions 22a, 22b is greater than 90 degrees. The probe members 12, 14, 16, 18 may also be formed from a single piece of material or formed from various components coupled together. The probe members 12, 14, 16, 18 may also have various cross-section shapes. For example, the embodiment of FIG. 1 has a rectangular cross-section while the embodiment of FIG. 3 has a circular cross-section. The probe members 12, 14, 16, 18 may be made from any of a variety of materials, such as, for example, dental grade metals (e.g., titanium, stainless steel, etc.) or plastics.

With continued reference to FIG. 3, the probe members 12, 14, 16, 18 are preferably configured and dimensioned such that one end of each pair of probe members 12, 14, 16, 18, respectively, serves as a probe end 26 of the dental implant guide 10 for contacting and/or probing the outer surface of the bone to receive the implant; whereas the opposite end of the respective pair of probe members 12, 14, 16, 18, respectively, serves as an indicator end 28 for indicating the contour of the bone and thereby the permitted limits for the dental implant. The probe members 12, 14, 16, 18 therefore form a set of four probe points A, B, C, D and a corresponding set of indicator points A', B', C', D'. Each probe point A, B, C, D corresponds to the indicator point A', B', C', D' that is located on the same probe member 12, 14, 16, 18. As will be explained in more detail below, in the illustrated embodiment, the envelope defined by the probe points A, B, C, D is generally symmetrical to the envelope defined by the indicator points A', B', C', D'.

The dental implant guide 10 illustrated in FIGS. 2 and 3 preferably also comprises a simulated tooth 30, which is configured to simulate the shape of an artificial tooth that is to be supported by the dental implant. The simulated tooth 30 is preferably configured for adjustment longitudinally, transversely, and/or angularly, with respect to the jawbone bone 2. In the illustrated embodiment, the simulated tooth 30 is coupled to the pivot shaft 13 by a support shaft 32 that may extend vertically from the pivot shaft 13. A horizontal member 34 extends in a substantially horizontal direction from the support shaft 32. The simulated tooth, in turn, may include a journal member 36 for receiving the horizontal member 34 such that the simulated tooth 30 may rotate about the horizontal member 34. The journal member 36 may, in turn, be configured for longitudinal movement within a longitudinal member support member 38. In one embodiment, the longitudinal member 38 and journal member 36 may include corresponding ratchet type structures for facilitating and limiting movement of the journal member 36 in the longitudinal direction. In other embodiments, the journal member 36 may be configured for sliding movement within the longitudinal member 38 with the amount of friction between the two component providing resistance to unlimited movement. Of course, those of skill in the art, will recognize that there are a variety of other mechanical relationships may be provided between the dental implant guide and the simulated tooth to provide adjustment, longitudinally, transversely and/or angularly with respect to the bone and dental implant guide 10. It should also be appreciated that modified embodiments (e.g., FIG. 1) of the tool guide 10 may be formed and used without the simulated tooth 30.

The simulated tooth 30 preferably includes one or more holes 40 therethrough to indicate the limits of the drill axis of the implant. As will be explained below, the hole 40 may be used for aligning the drill therethrough or other dental components (e.g., an angled abutment).

With reference back to FIG. 2, the dental implant guide 10 may include one or more biasing members 42a, 42b (e.g., springs) applied to the indicator end of one or both pairs of probe members 12, 14, 16, 18 for urging the indicator points A', B', C', D' and the respective probe members 12, 14, 16, 18 towards each other. Thus, as shown in FIG. 3, a first spring 42a urges the first pair of probe members 12, 14 towards each other, and a second spring 42b urges the second pair of probe members 16, 18 towards each other. It should be appreciated that in other embodiments other techniques may be used for urging the respective probe members 12, 14, 16, 18 towards each other. For example, in one embodiment, a torsional spring may be applied to the probe members 12, 14, 16, 18 at the pivot shaft 13.

With reference back to FIG. 3, a manner in which the exemplary dental implant guide 10 may be used to aid the oral surgeon in determining the optimum position and angle for installation of a dental implant according to the contour of the bone at the site to receive the implant will now be described in more detail. As mentioned above, in the illustrated embodiment, the first pair of probe members 12, 14 are substantially the same shape and length, and the second pair of probe members 16, 18 are also substantially the same shape and length of each other. However, as mentioned above, the second pair of probe members 16, 18 preferably have a height less than the first pair of problem members 12, 14. As mentioned above, the exemplary dental implant guide 10 creates four probe points A, B, C, D that indicate the contour of the bone 2 at the implantation site, and thereby provides four indicator points A', B', C', D' in space over the implantation site to assist the oral surgeon in determining the optimum position and angle for the dental implant to be installed at that site. In the illustrated embodiment, the first and second pair of probe members 12, 14, 16, 18 are substantially symmetrical with respect to the pivot shaft 13. Therefore, the spatial relationship between the four indicator points A', B', C', D' is substantially symmetrical to the spatial relationship between the four probe points A, B, C, D. It will be appreciated that more than two pairs of such probe members could be included in the accessory, to provide more probe points indicating the contour of the bone, and thereby more guide points for assisting the oral surgeon in determining the optimum placement of the dental implant. It should also be appreciated that one pair of probe members may also be used in other embodiments.

In use, even before the bone site to receive the implant has been flapped, the dental implant guide 10 may be positioned at the implantation site with the pivoted point 13 of the accessory being positioned in close proximity to the ridge of the bone 2, and with the probe points A, B, C, D of the probe members 12, 14, 16, 18 respectively, in contact with or close proximity to the opposite faces of the bone 2, as shown at 2A, 2B, 2C, 2D, respectively (see FIG. 3). The probe points A, B, C, D thus indicate the contour of bone 2 at the implantation site and are reproduced in the illustrated embodiment as the indicator points A', B', C', D' respectively, at the opposite ends of the probe members 12, 14, 16, 18 in the space overlying the implantation site. The oral surgeon thus can visualize the space, symmetrically below the pivot shaft 13, available for positioning and orientating the implant. For safety purposes, the indicator points A', B', C', D' are preferably positioned a small distance inwardly from a position that would exactly correspond to the probe points A, B, C, D. This may be accomplished by dimensioning the tertiary members 24b of the indicator end 28 to be slightly longer than the tertiary members 24a of the probe end 26 or providing extensions 44 as shown in FIG. 3. In some embodiments, the extensions 44 be configured with enhanced indicia (e.g., bright colors) to aid the surgeon in visualizing the envelope.

As shown in FIG. 3A, when the axis a of an implant or drill is positioned within the envelop defined by the indicator points A', B', C', D', it is at a position, orientation and angle that when extended into the bone 2 ensures that the implant or drill will remain within the contours of the bone.

With embodiments that utilize the simulated tooth 30 (see e.g., FIG. 3), the oral surgeon may also manipulate the simulated tooth 30 to obtain the desired relationship with respect to a counter-tooth 46. For this purpose, the simulated tooth 30 may be moved longitudinally, transversely, and/or angularly, with respect the pivot shaft 13, and thereby with respect to the bone 2. The hole 40 in the simulated tooth 30 is located so as to indicate the limits of the drill axis of the implant when the simulated tooth 30 is properly oriented with respect to the counter tooth 46. In other embodiments, the simulated tooth 30 may include additional holes to indicate the axis of mating components (e.g., an angled abutment) A drill bit may be positioned through the hole 40, which may be used for aligning the drill bit. For a particular position and orientation of the drill, if the proximal end of the drill bit lies within the envelop defined by the indicator points A', B', C', D', then the oral surgeon knows that if the drill is extended along the same axis it will remain within the envelop defined by the contact points A, B, C, D.

In certain embodiments, the dental implant guide 10 is configured such that the indicator points A', B', C', D' provide an accurate representation of the contour of the bone 2. However, it should be appreciated that in modified embodiments, the dental implant guide 10 may be configured such that indicator points A', B', C', D' provide only general or approximate info with respect to the contour of the bone. For example, in one embodiment, the indicator points A', B', C', D' may merely indicate the general thickness of the bone 2 and, in another, embodiment merely indicate the general thickness of the bone at an approximated depth. In such embodiments, the probe members 12, 14, 16, 18 need not be symmetric with respect to the pivot axis.

From the description above, it should be apparent that the dental implant guide 10 is highly useful for guiding the oral surgeon in the placement of the implant at its optimum position and angle for the respective dental prosthesis to be subsequently applied. In addition, in the embodiments with two such pairs of probe members of different heights, the lower end of each probe assembly is particularly suited to probe the contour of the bone at the implant installation site, and thereby better able to guide the oral surgeon in the placement of the implant. The oral surgeon may also use the dental implant guide 10 to determine that in the desired orientation the dental implant will lies outside the permitted limits. Accordingly, the dental implant guide aids the surgeon in determining that a bone graft is needed and may aid the surgeon in deciding the size and placement of the bone graft. The dental guide 10 may also be used to control and monitor the success of the bone graft during, for example, the months following the bone graft procedure.

Figure 4:
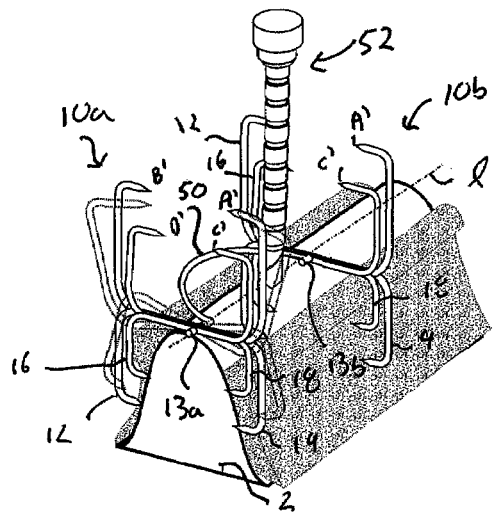
FIG. 4 is a side perspective view of an embodiment of that utilizes two connected dental implant guides.

FIG. 4 illustrates a modified embodiment that includes two dental implant guides, generally designated 10a, 10b, each including two pairs of probe members 12, 14, 16, 18 respectively, as described above. The two dental implant guides 10a, 10b, are spaced from each other and coupled together by a common bridging member 50. In the illustrated embodiment, the common bridging member 50 bows away from a longitudinal axis extending through the pivot shafts 13a, 13b of the dental implant guides 10a, 10b to provide access for a dental implant 52 that may be positioned between the dental implant guides 10a, 10b. In this embodiment, with the dental implant 52 positioned between the dental implant guides 10a, 10b, the probe points A, B, C, D at the probe end of the two probe assemblies will indicate the contour of the bone 2 between the two probe assemblies, and thereby the opposite ends of the probe members will better indicate the contour of the bone in this region.

Figure 5:
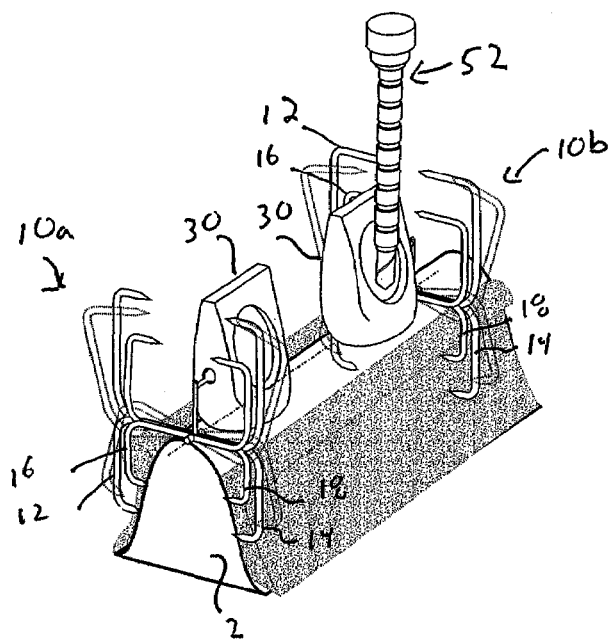
FIG. 5 illustrates the use of a plurality of the dental implant guides of FIG. 2.

FIG. 5 also illustrates another modified embodiment that includes two dental implant guides, generally designated 10a, 10b, each including two pairs of probe members 12, 14, 16, 18 respectively, as described above. In this embodiment, each dental implant guide 10a, 10b, includes a simulated tooth 30. In one embodiment of use, the pair of dental implant guides 10a, 10b may be use to probe the contour of the bone in the region to receive two implants, such as region 8 illustrated in FIG. 1. In modified embodiments the dental implant guides 10a, 10b may be used without the simulated tooth 30.

Figure 6:
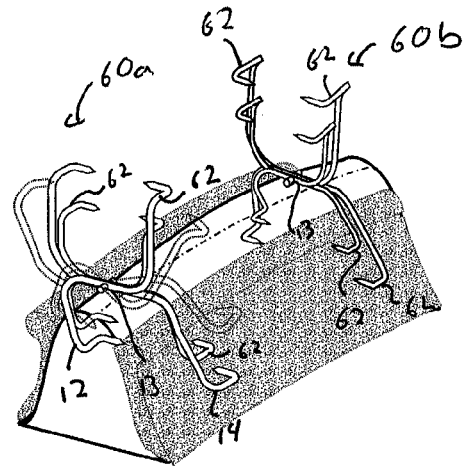
FIG. 6 is a side perspective view of another embodiment of a dental implant guide.

FIG. 6 illustrates another modified embodiment of a pair of dental implant guides 60a, 60b. In the previous embodiments, the probe members 12, 14, 16, 18 were configured such that the indicator points A', B', C', D' and the probe points A, B, C, D, were positioned substantially within the same plane as the pivot shaft 13. In the present embodiment, the probe points A, B, C, D and indicator points A', B', C', D may be positioned within different planes or in a common plane offset from a plane containing the pivot shaft 13. In the illustrated embodiment, this is accomplished by providing the tertiary members 24a, 24b with an offset portion 62. In the exemplary embodiment, the offset portions 62 extend generally parallel to the axis of the pivot shaft 13. In this manner, the probe points A, B, C, D and indicator points A', B', C', D' are distanced from the pivot shaft 13. This arrangement allows the surgeon to position the implant or drill directly between the indicator points A', B', C', D'.

Figure 8:
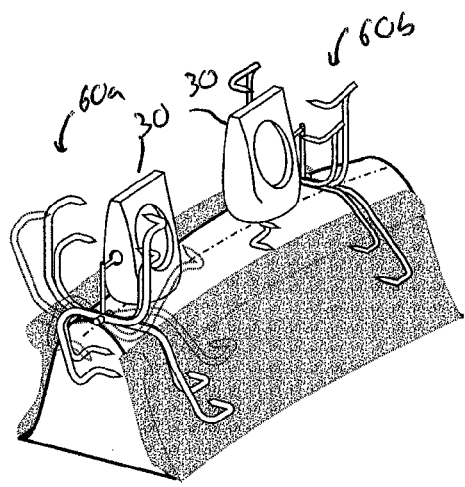
FIG. 8 illustrates the use of a plurality of the dental implant guides in FIG. 6 in combination with a simulated tooth.
Figure 7:
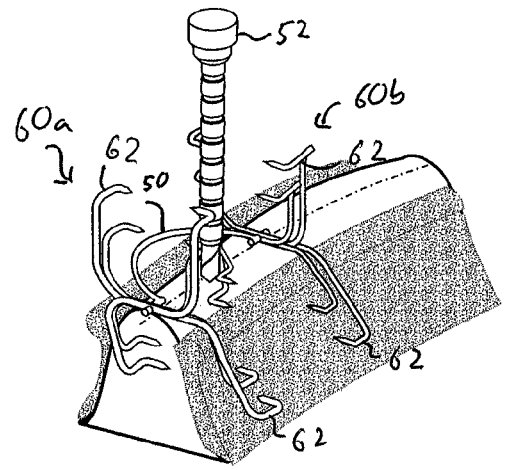
FIG. 7 illustrates an embodiment of use of a pair dental implant guides as shown in FIG. 6 wherein the dental implant guides are connected.

FIG. 7 illustrates a modified embodiment of the dental implant guides 60a, 60b of FIG. 6. In this embodiment, the dental implant guides 60a, 60b are coupled together with a common bridging member 50 as described above with reference to FIG. 4. FIG. 8 illustrates another modified embodiment of the dental implant guides 60a, 60b of FIG. 6. In this embodiment, the dental implant guides 60a, 60b are used with a simulated tooth as described above with reference to FIG. 4.

Figure 9:
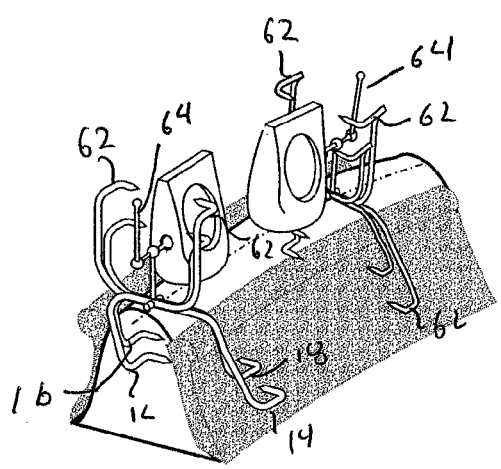
FIG. 9 illustrates the use of a plurality of the dental implant guides in FIG. 6 in combination with a simulated tooth and an indicator rod.

FIG. 9 illustrates another modified embodiment of the dental implant guides 60a, 60b of FIG. 8. In this embodiment, each of the simulated teeth 30 includes an indicator pin 64 mounted to the horizontal shaft 34. The indicator pin 64 indicates the drilling axis through the hole 40 of the respective simulated tooth. This arrangement aids the oral surgeon in assuring that the drilling axis of the two simulated teeth implants are parallel to each other, before and/or during drilling.

The dental implant guides described above are preferably supplied to the oral surgeon in the form of a kit having a number of such accessories of different sizes In one embodiment, the kit may include a plurality of dental implant guides of different sizes in order to accommodate a wide range of bone structures. Such a kit preferably would also include a tool, such as shown in FIG. 10 and described below, for conveniently applying and removing the accessories.

Figure 10:
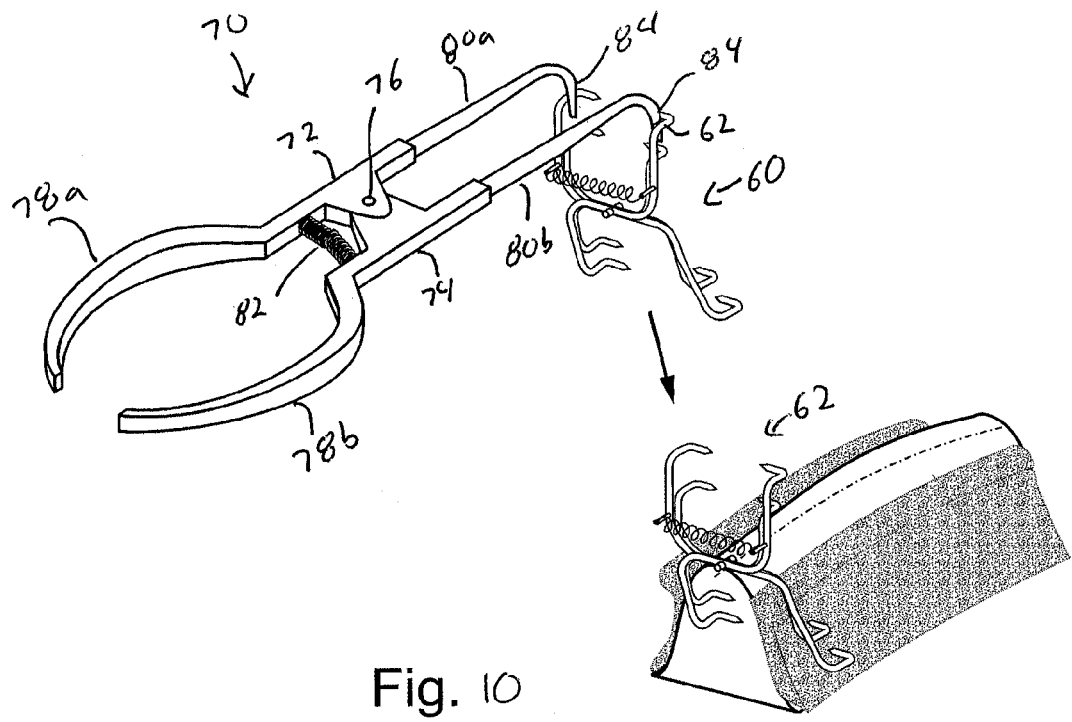
FIG. 10 is a side perspective view of an exemplary embodiment of a tool that may be used with the dental implant guides of FIGS. 6 and 7.

With reference now to FIG. 10, an exemplary embodiment of a tool 70 that may be used in combination with a dental implant guide will now be described. The tool 70 includes a pair of members 72, 74 pivotally mounted to each other at pivot axis 76. The proximal end of the members 72 are formed with hand grips 78a, 78b on one side of the pivot axis 76 while the distal end on the opposite side of the pivot axis 76 is formed with elongated fingers 80a, 80b. A biasing member 82 (e.g., a spring) is preferably provided between the hand grips 78a, 78b to urge the hand grips 78a, 78b away from each other, and thereby the fingers 80a, 80b towards each other.

A dental practitioner may grip the tool 70 by the hand grips 78a, 78b and guide the two fingers 80a, 80b between one or both pairs of the probe members 12, 14, 16, 18. In one embodiment, the fingers 80a, 80b engage the shorter of the pair of probe members 12, 14, 16, 18 such that both pair of members may be expanded upon squeezing the two hand grips 78a, 78b. The dental implant guide 62 may then been be positioned on the bone 2 with the probe end 26 straddling the bone 2. To remove the dental implant guide 60, the two fingers 80a, 80b may be positioned between one or both pairs of the probe members 12, 14, 16, 18 and expanded such that the dental implant guide may be moved away from the bone 2. This embodiment is particularly configured to be used with the dental implant guides 60a, 60b of FIGS. 6-9. Accordingly, the fingers 80a, 80b include downwardly projecting members 84 that are configured to engage the offset portions 62 of the dental implant guides 60a, 60b.

Figure 11:
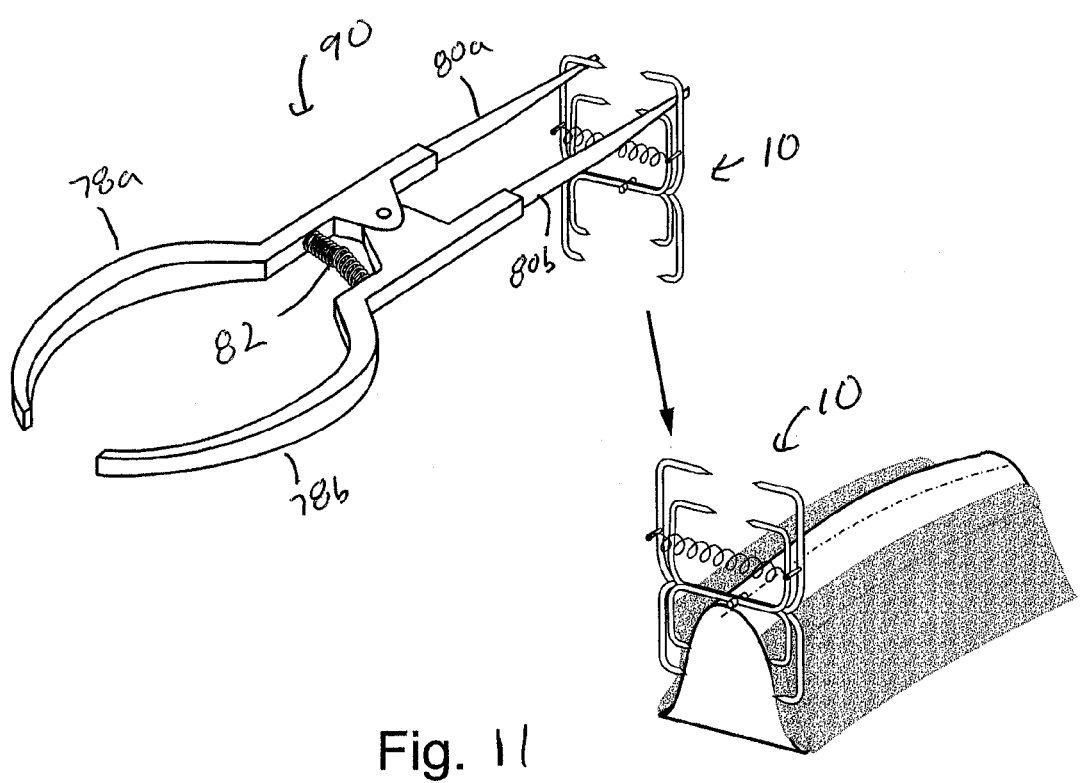
FIG. 11 is a side perspective view of an exemplary embodiment of a tool that may be used with the dental implant guides of FIGS. 1-5.

FIG. 11 illustrates a tool 90 of similar construction as the tool 80 of FIG. 10 and accordingly similar reference numbers have been used to refer to components that are similar to the embodiment of FIG. 10. This embodiment is particularly configured for embodiments in which the indicator points are not offset from the pivot shaft 13 (e.g., the embodiments of FIGS. 1-5). Accordingly, the fingers 80a, 80b do not include downwardly projecting members 84.

Figure 12:
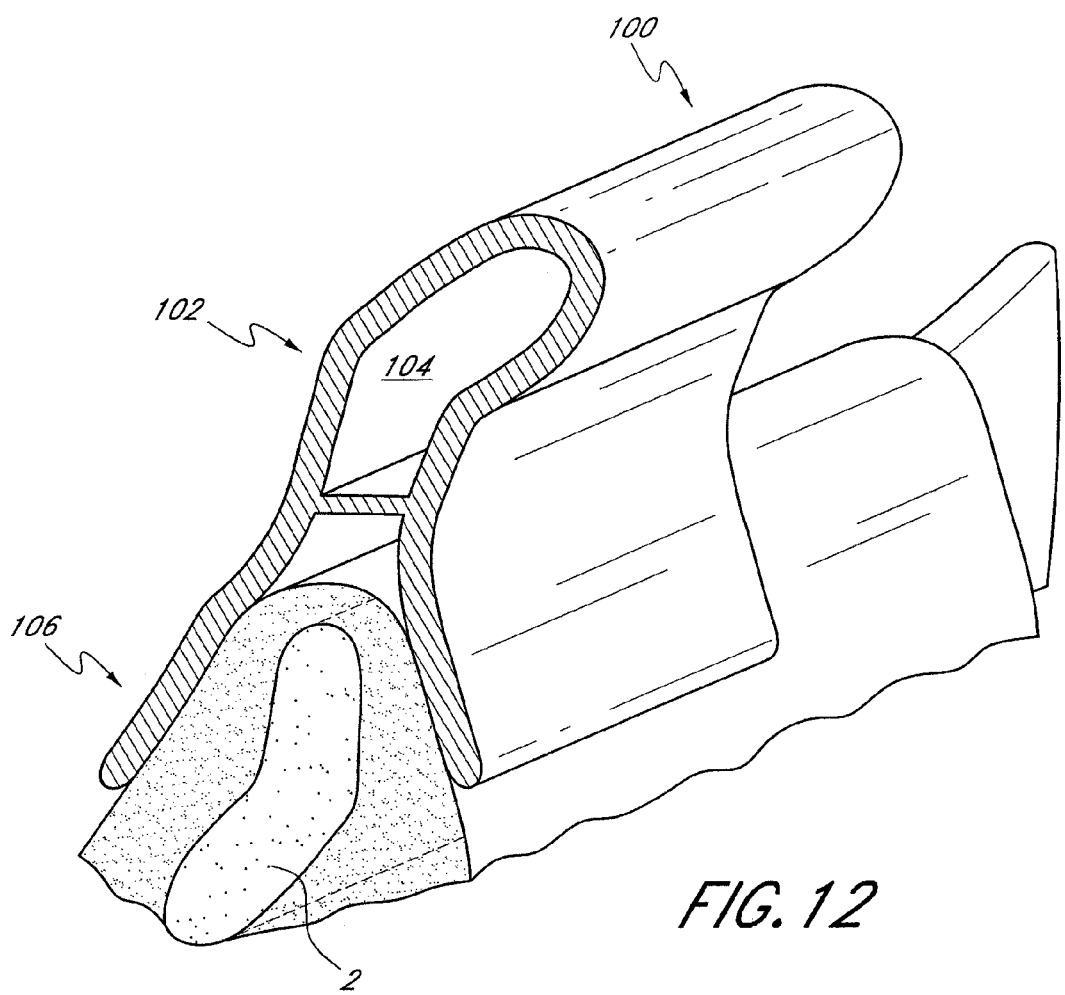
FIG. 12 is a side perspective view of a modified embodiment of a dental implant guide.
Figure 12A:
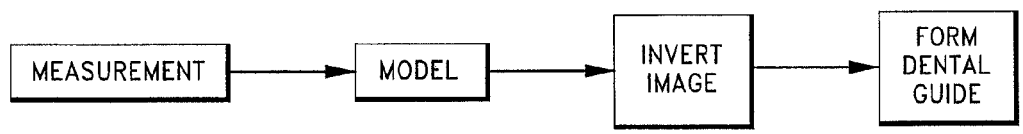
FIG. 12A is a flow chart illustrating one embodiment for creating the dental implant guide of FIG. 12.
Figure 13:
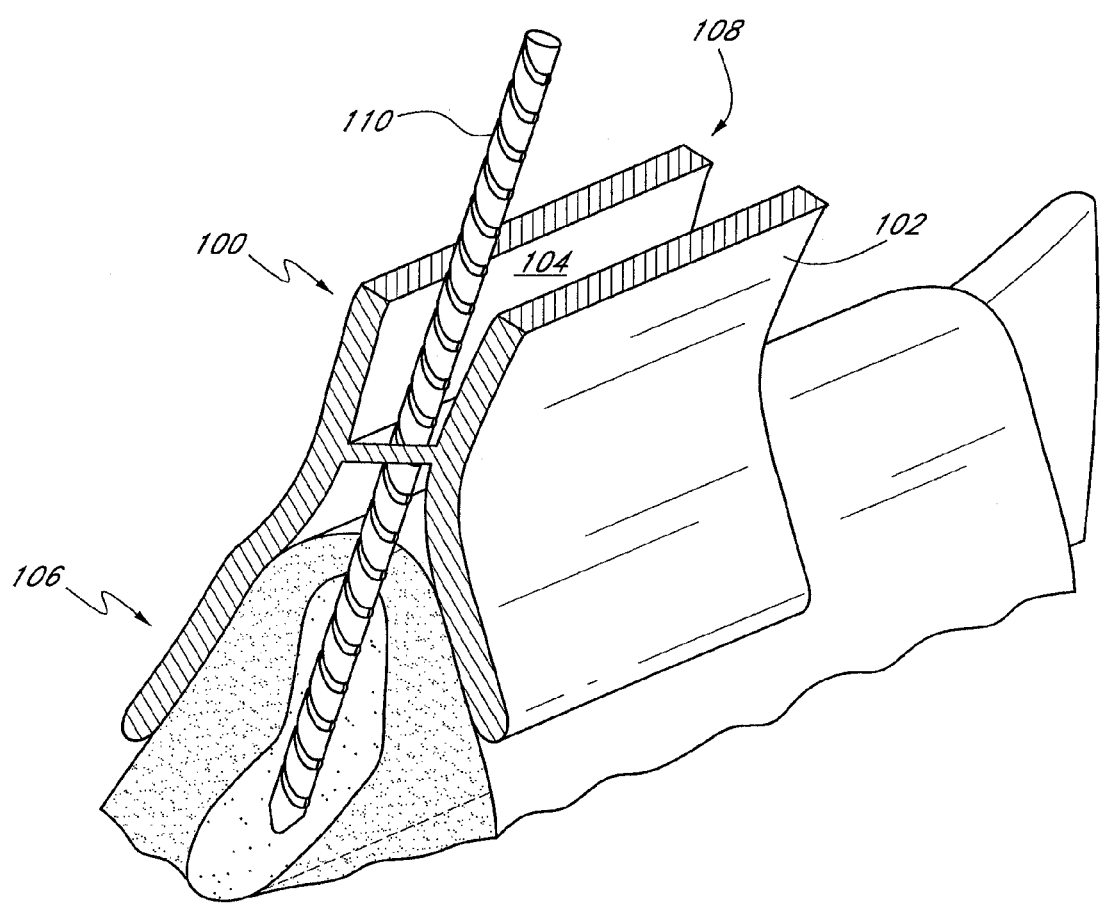
FIG. 13 is a side perspective view of a modified embodiment of the dental implant guide of FIG. 12.

FIGS. 12 and 13 illustrated another embodiment of a dental implant guide 100. With reference to FIG. 12A, in one embodiment, the dental guide is formed by taking measurments of the patient's mouth. With continued reference to FIG. 12A, the measurements are used to create a physical or computer model of a patient's mouth using various known techniques. (See e.g., the interactive CT software sold under the trademark SimPlant by Materialise NV). In one embodiment, the physical model may be based upon an impression taken of the patient's mouth. In another embodiment, a computer model of the patient's mouth may be generated from a CT scan or x-ray. The model is used to determine the shape and contour of the bone or/and the gum or/and the teeth around the insertion site. As shown in FIG. 12A, the image of jawbone may then inverted to create a symmetrical image of the bone including anatomic landmarks but in some embodiments also axes, paths and/or contours of the definitive prosthesis above the insertion site with the image preferably centered about the center of the bone with the center of symmetrical ideally positioned on the middle of the crest bone. A three-dimensional dental implant guide 100 (see FIG. 12) can then be created from the model. Various techniques may be used to form the dental implant guide, such as, for example milling, injection molding techniques, investment casting etc.

As shown in FIG. 12, the dental implant guide 100 includes an upper portion 102 defining a cavity 104 that corresponds to the shape of the symmetrical image or slightly smaller version of the symmetrical image. The lower portion 106 may be configured to fit over the insertion site such that the symmetrical image is positioned generally over the insertion site. An opening (see FIG. 13) may be formed in the dental implant guide 100 such that an implant or drill 110 may be positioned in the guide 100 over the insertion site. The orientation of the implant or drill 110 may be adjusted within a physical representation of the envelope and anatomic landmark defined by the dental implant guide 100 to ensure the proper orientation avoiding the anatomic landmarks like dental nerve or sinus or the roots of contiguous teeth.

While the invention has been described with respect to several preferred embodiments, it will be appreciated that these are set forth merely for purposes of example, and that many variations may be made. For example, the probe assemblies may be provided with more than two pairs of pivot members in order to increase the number of contact points with the bone, and thereby to provide a more precise indication of the contour of the bone for aiding the oral surgeon to determined the optimum position and angle for installing the dental implant. Similarly, an accessory may include more than two such probe assemblies in order to provide an indication of the bone contour for a longer region of the bone.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combination or sub-combinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A method of determining the physical limits that a jawboned provides when installing a dental implant in the jawbone, the method comprising:
   determining the contour of the jawbone at an insertion site of the dental implant;
   creating a three dimensional dental implant guide, which is a substantially symmetrical and inverted image of the contour of the jawbone;
   positioning said dental implant guide above said insertion site; and
   using said dental implant guide to determine an envelope for a dental drill to drill into the jawbone to install the dental implant.

2. The method of claim 1, wherein the step of creating a three dimensional dental implant guide comprises determining the contour of anatomic landmarks at the insertion site and creating a substantially symmetrical and inverted image of the contour of the anatomical landmark at the insertion site.

3. The method of claim 1, wherein the step of creating a three dimensional dental implant guide comprises determining the contour of contiguous roots at the insertion site and creating a substantially symmetrical image of the contour of the contiguous roots at the insertion site.

4. The method of claim 1, wherein the step of determining the contour of the jawbone comprises probing opposite sides of the bone.

5. The method of claim 1, wherein the step of determining the contour of the jawbone comprises establishing at least two contact points on opposite sides of the bone.

6. The method of claim 5, wherein the step of creating the dental implant guide comprises establishing at least two indicator points that substantially correspond to the at least two contact points above the insertion site.

7. The method of claim 1, wherein the step of determining the contour of the jawbone comprises taking a CT scan.

\* \* \* \* \*